US012745909B2

(12) United States Patent
Yamamoto et al.

(10) Patent No.: US 12,745,909 B2
(45) Date of Patent: Sep. 29, 2026

(54) BLOOD VESSEL VISUALIZATION APPARATUS, BLOOD VESSEL PUNCTURE SYSTEM, AND OBSERVATION WINDOW MEMBER

(71) Applicant: TERUMO KABUSHIKI KAISHA, Tokyo (JP)

(72) Inventors: Shota Yamamoto, Mitaka (JP); Takayuki Yokota, Chuo (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 632 days.

(21) Appl. No.: 18/108,190

(22) Filed: Feb. 10, 2023

(65) Prior Publication Data

US 2023/0190191 A1 Jun. 22, 2023

Related U.S. Application Data

(63) Continuation of application No. PCT/JP2021/030495, filed on Aug. 20, 2021.

(30) Foreign Application Priority Data

Aug. 26, 2020 (JP) ................................ 2020-142281

(51) Int. Cl.
*A61B 5/00* (2006.01)
*A61B 5/15* (2006.01)
(Continued)

(52) U.S. Cl.
CPC .......... *A61B 5/0077* (2013.01); *A61B 5/0059* (2013.01); *A61B 5/15003* (2013.01);
(Continued)

(58) Field of Classification Search
CPC ..... A61B 5/489; A61B 5/0059; A61B 5/0077; A61B 5/15003; A61B 5/150748;
(Continued)

(56) References Cited

U.S. PATENT DOCUMENTS 5,519,208 A * 5/1996 Esparza ............ A61B 5/15003 250/341.8
2006/0176242 A1* 8/2006 Jaramaz ............... G02B 27/017 345/7
2016/0157774 A1* 6/2016 Goldman ............... A61B 5/489 600/473

FOREIGN PATENT DOCUMENTS

EP 2042084 A1 * 4/2009 ........... A61B 5/0059
GB 2542132 A * 3/2017 ........... A61B 5/6898
(Continued)

OTHER PUBLICATIONS

International Searching Authority, "Written Opinion," issued in connection with International Patent Application No. PCT/JP2021/030495, dated Nov. 9, 2021.
(Continued)

*Primary Examiner* — Wesley G Harris
(74) *Attorney, Agent, or Firm* — Foley & Lardner LLP

(57) ABSTRACT

A blood vessel visualization apparatus, a blood vessel puncture system, and an observation window member include: light sources that irradiate with near infrared light a visualization target site; an observation window that contains a wavelength conversion material for converting the near infrared light into visible light; a frame member that holds the observation window; and support members that support the frame member apart from the visualization target site. The observation window visualizes an image of near infrared light radiated from the light sources and reflected by the visualization target site.

13 Claims, 5 Drawing Sheets

(51) Int. Cl.
*A61M 5/00* (2006.01)
*A61B 17/34* (2006.01)

(52) U.S. Cl.
CPC .. *A61B 5/150748* (2013.01); *A61B 5/150824* (2013.01); *A61B 5/489* (2013.01); *A61M 5/00* (2013.01); *A61B 17/34* (2013.01)

(58) Field of Classification Search
CPC ... A61B 5/150824; A61B 17/34; A61B 5/742; A61M 5/00; A61M 5/427; H04N 23/21
See application file for complete search history.

(56) References Cited

FOREIGN PATENT DOCUMENTS

| | | | | | |
|---|---|---|---|---|---|
| JP | 2002-345953 | A | | 12/2002 | |
| JP | 2008-167792 | A | | 7/2008 | |
| JP | 2010-148853 | A | | 7/2010 | |
| JP | 2011-160891 | A | | 8/2011 | |
| JP | 2012532682 | A | * | 12/2012 | ............. A61B 90/37 |
| JP | 2015-033585 | A | | 2/2015 | |
| JP | 2017064094 | A | * | 4/2017 | ............ A61M 5/427 |
| WO | WO-2009049633 | A1 | * | 4/2009 | ....... A61B 5/150824 |

OTHER PUBLICATIONS

Funabashi et al., “A Solid Material That Converts Near-Infrared Light to Visible Light Realized by a Solution Coating Method,” National Institute of Advanced Industrial Science and Technology, dated May 30, 2019, URL: https://www.aist.go.jp/aist_j/press_release/pr2019/pr20190530_2/pr20190530_2.html.
International Searching Authority, “International Search Report,” issued in connection with International Patent Application No. PCT/JP2021/030495, dated Nov. 9, 2021.
Office Action issued in Japanese Appl. No. 2022-544530 dated Jan. 21, 2025.

* cited by examiner

BLOOD VESSEL VISUALIZATION APPARATUS, BLOOD VESSEL PUNCTURE SYSTEM, AND OBSERVATION WINDOW MEMBER

CROSS-REFERENCE TO RELATED APPLICATIONS

This application is a bypass continuation of PCT Application No. PCT/JP2021/030495, filed on Aug. 20, 2021, which claims priority to Japanese Application No. JP2020-142281, filed on Aug. 26, 2020. The contents of these applications are incorporated by reference in their entireties.

BACKGROUND

The present invention relates to a blood vessel visualization apparatus, a blood vessel puncture system, and an observation window member that irradiate a living body with near infrared light and visualize blood vessels.

A medical worker performs a procedure of puncturing a patient's blood vessel with a puncture needle such as an indwelling needle. It is demanded to improve a puncture success rate by making it possible to identify a blood vessel having an appropriate thickness, and reliably insert the puncture needle into a blood vessel of interest when performing puncturing with a puncture needle.

In order to improve such the puncture success rate, there have been proposed various blood vessel visualization apparatuses that can irradiate a puncture target site with near infrared light having high permeability with respect to a living body, and identify a course of a blood vessel.

For example, a blood vessel visualization apparatus disclosed in Japanese Patent Application Laid-Open No. 2017-64094 A is configured such that light sources irradiate a patient's puncture target site with near infrared light, image capturing means captures a near infrared light image reflected by the puncture target site, and a liquid crystal display apparatus visualizes and displays the captured near infrared light image.

SUMMARY

However, the conventional blood vessel visualization apparatus has a problem that an apparatus configuration such as image capturing means and a liquid crystal display apparatus is necessary, and the apparatus configuration becomes complicated and large.

Therefore, a blood vessel visualization apparatus, a blood vessel puncture system, and an observation window member that can visualize blood vessels with a simpler apparatus configuration are desired.

According to one aspect of the present disclosure, a blood vessel visualization apparatus includes: a light source that irradiates with near infrared light a visualization target site at which a blood vessel of a living body is visualized; an observation window that contains a wavelength conversion material for converting the near infrared light into visible light, and visualizes a near infrared light image reflected from the visualization target site; and a support member that supports the light source and the observation window such that the light source and the observation window face and are spaced apart from the visualization target site.

According to another aspect of the present disclosure, a blood vessel puncture system includes: the blood vessel visualization apparatus according to the above aspect; and a medical tool that includes a puncture portion that can puncture a blood vessel.

According to another aspect of the present disclosure, an observation window member of a blood vessel visualization apparatus that includes a light source that irradiates with near infrared light a visualization target site at which a blood vessel of a living body is visualized, and an observation window that contains a wavelength conversion material for converting the near infrared light into visible light, and visualizes a near infrared light image reflected from the visualization target site, and is the observation window member that includes: the observation window that is arranged facing the visualization target site; a frame member that holds the observation window; and a support member that supports the frame member spaced apart from the visualization target site.

The blood vessel visualization apparatus, the blood vessel puncture system, and the observation window member according to the above aspects can visualize blood vessels with a simpler apparatus configuration.

DETAILED DESCRIPTION

Hereinafter, preferred embodiments of the present invention will be described in detail with reference to the accompanying drawings.

First Embodiment

Figure 1:
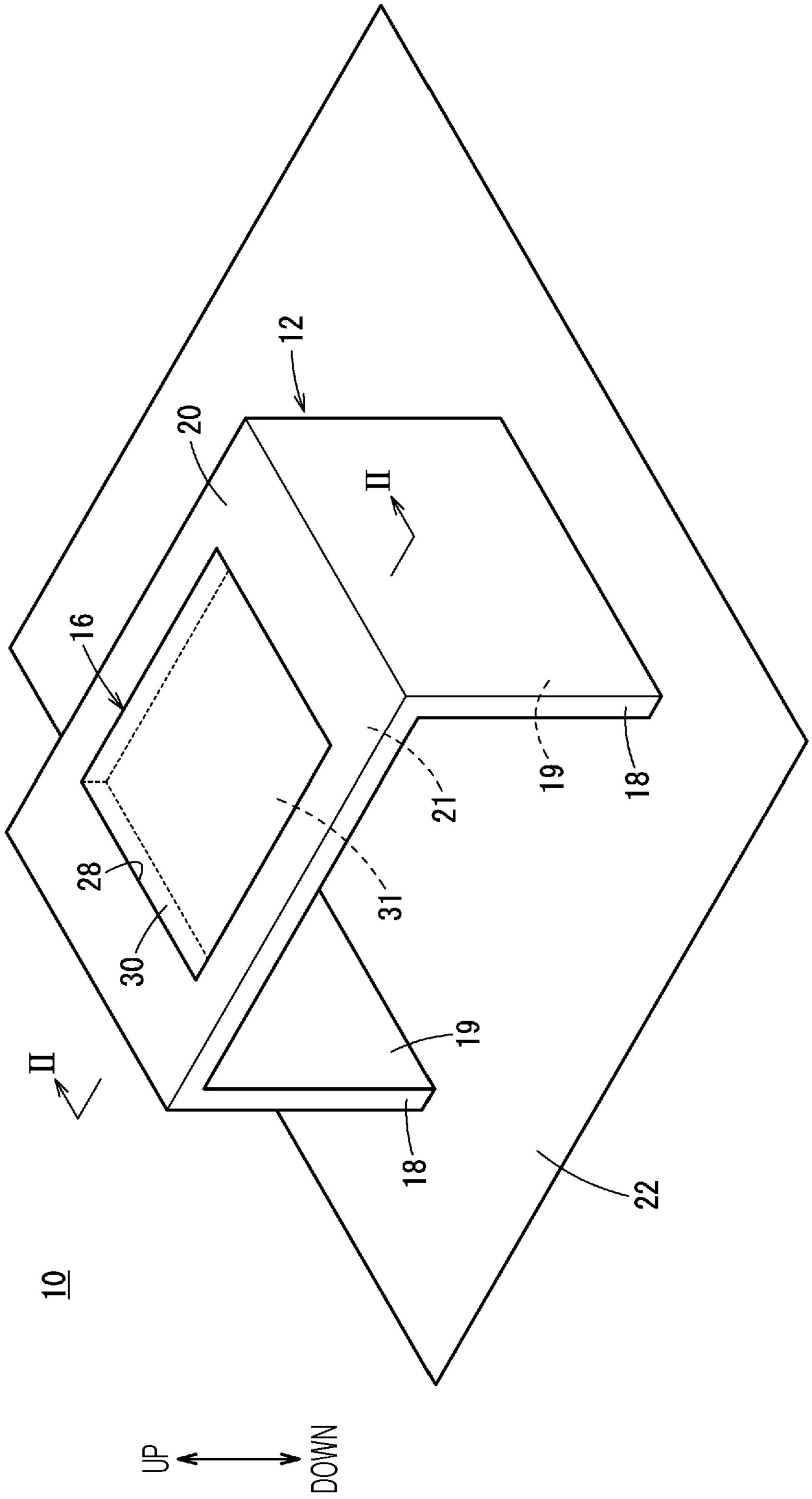
FIG. 1 is a perspective view of a blood vessel visualization apparatus according to a first embodiment.
Figure 2:
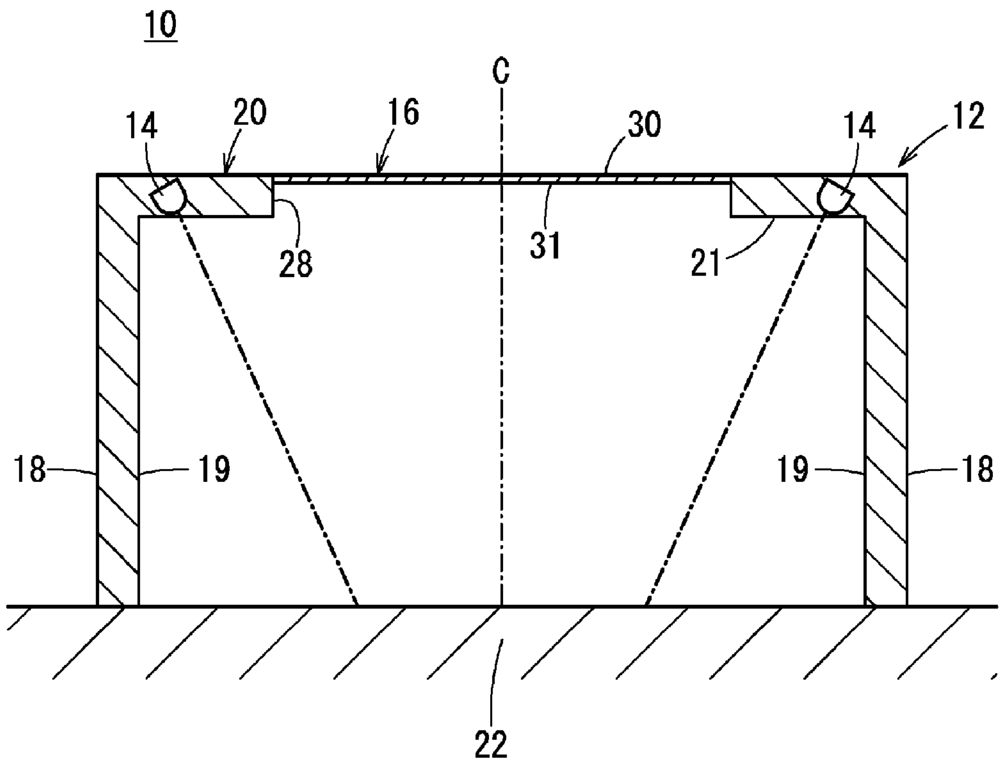
FIG. 2 is a cross-sectional view taken along a line II-II of the blood vessel visualization apparatus in FIG. 1.

As illustrated in FIGS. 1 and 2, a blood vessel visualization apparatus 10 according to the present embodiment includes a box-shaped observation window member 12, and light sources 14 and an observation window 16 supported by this observation window member 12. The observation window member 12 includes a pair of plate-like support members 18, and a plate-like frame member 20 provided so as to be bridged between the support members 18.

The support members 18 support the frame member 20 such that the frame member 20 is substantially parallel to a flat support base 22, such as a top surface of a work table, when lower end portions of the support members 18 are placed on the support base 22. The support members 18 keep a state where the frame member 20 and the support base 22 are spaced apart from each other. A separation distance between the frame member 20 and the support base 22 is determined by heights of the support members 18.

A space between the frame member 20 and the support base 22 is configured to form a distance at which the visualization target site 24 at which a blood vessel 25 of a living body is visualized can be arranged. The heights of the support members 18 are preferably set such that, when the visualization target site 24 as illustrated in FIG. 4 is arranged between the frame member 20 and the support base 22, a puncture space 27 that enables a medical tool 26 such as a puncture needle or a catheter assembly to perform puncturing can be formed between the visualization target site 24 and the frame member 20.

Figure 4:
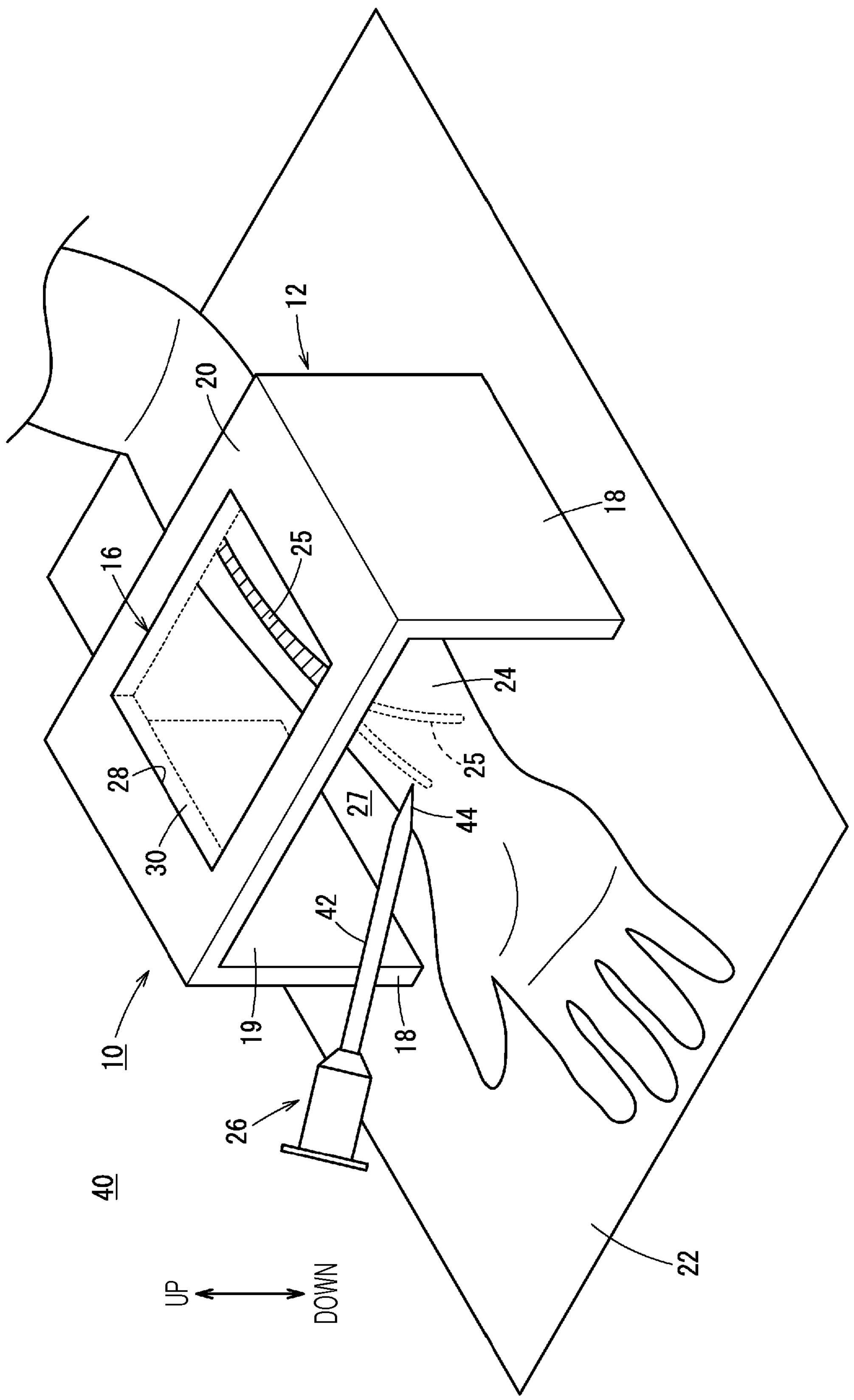
FIG. 4 is an explanatory view of a blood vessel puncture system including the blood vessel visualization apparatus in FIG. 1.

The visualization target site 24 is not particularly limited, but may be a patient's arm as illustrated in FIG. 4. Furthermore, in a case where the visualization target site 24 is an arm, the heights of the support members 18, that is, the separation distance between the support base 22 and the frame member 20 can be set to, for example, approximately 10 to 20 cm. In addition, the separation distance (the heights of the support members 18) between the support base 22 and the frame member 20 is not limited to the above numerical range, and can be appropriately adjusted.

Inner surfaces 19 of the support members 18 on the visualization target site 24 side may be covered with a near infrared light absorbing material having a high light absorption rate of near infrared light to prevent diffused reflection of the near infrared light. Furthermore, a bottom surface 21 of the frame member 20 on the visualization target site 24 side may also be covered with the near infrared light absorbing material similarly to the inner surfaces 19 of the support members 18. The support members 18 and the frame member 20 may be formed by a light shielding material that does not allow visible light to pass to limit entry of the visible light from the outside.

A rectangular opening portion 28 is formed in the frame member 20 of the observation window member 12. The opening portion 28 penetrates the frame member 20 in a thickness direction. The observation window 16 is fitted and joined to the opening portion 28 of the frame member 20. The observation window 16 includes a rectangular plate member 30 formed to have dimensions that can be fitted into the opening portion 28. The thickness of the plate member 30 is not particularly limited, yet is formed equally to the thickness of the frame member 20 or thinner than the thickness of the frame member 20.

As illustrated in FIG. 2, the bottom surface 31 of the plate member 30 is preferably arranged at a position recessed toward an upper side of the bottom surface 21 of the frame member 20 in order to prevent light emitted from the light sources 14 from directly entering the plate member 30. According to this configuration, it is possible to reduce entry of near infrared light as a noise component, and project a clearer visualized image (visible light image) of the blood vessel 25 on the observation window 16.

The surface of the plate member 30 is applied a wavelength conversion material that converts near infrared light of 700 to 1100 nm into visible light. The wavelength conversion material that converts near infrared light into visible light is also referred to as an up-conversion material, and is, for example, a material of Japanese Patent Application Laid-Open No. 2019-172992 A.

As an up-conversion material, a material containing, in molecules, a sensitizer that absorbs light of a long wavelength and efficiently generates a triplet, and an emitter that generates an excited triplet of a long life span by triplet-triplet energy transfer (TTET) from the sensitizer, further generates an excited singlet by excited triplet-triplet collision, and thereby emits fluorescence can highly efficiently convert near infrared light into visible light, and therefore is gaining attention. The observation window 16 containing the material that can highly efficiently convert near infrared light into visible light visualizes an image of the near infrared light reflected inside the living body with visible luminance.

The observation window 16 is transparent or semitransparent with respect to visible light, and makes it possible to directly visually check by means of the visible light the visualization target site 24 such as an arm irradiated with the visible light having entered a gap between the observation window member 12 and the visualization target site 24. When the light sources 14 are turned on, a near infrared light image is superimposed on a visible light image of light entering from the outside to visibly project the blood vessel 25.

The observation window 16 is not limited to an observation window obtained by applying a wavelength conversion material to the surface of the plate member 30 made of a plate-like transparent material (resin or glass). The observation window 16 may be formed by dispersing a wavelength conversion material in a transparent material that forms the plate member 30. In addition, the observation window 16 is not limited to the plate member 30, and may be a wavelength conversion film obtained by containing or applying a wavelength conversion material in or to a resin film having flexibility.

As illustrated in FIG. 2, the light sources 14 are provided on the bottom surface 21 side of the frame member 20, and irradiate a space below the observation window 16 with near infrared light. The light source 14 is an infrared light emitting LED element or an infrared laser oscillation element that emits near infrared light, and emits near infrared light of 700 to 1100 nm. The near infrared light in this wavelength band is excellent in permeability to living tissues, but is easily absorbed by red blood cells. The near infrared light from the light source 14 is absorbed more at a portion of the blood vessel 25 containing many red blood cells when reflected by the living tissues of the visualization target site 24, and therefore generates a near infrared light image that reflects the shape of the blood vessel 25 in the reflected light.

The light source 14 is attached to the frame member 20 such that a center (optical axis) of an irradiation range of the light source 14 is inclined toward an axis C that passes through a center of the observation window 16. Consequently, it is possible to efficiently irradiate with near infrared light the visualization target site 24 arranged below the observation window 16.

Figure 3:
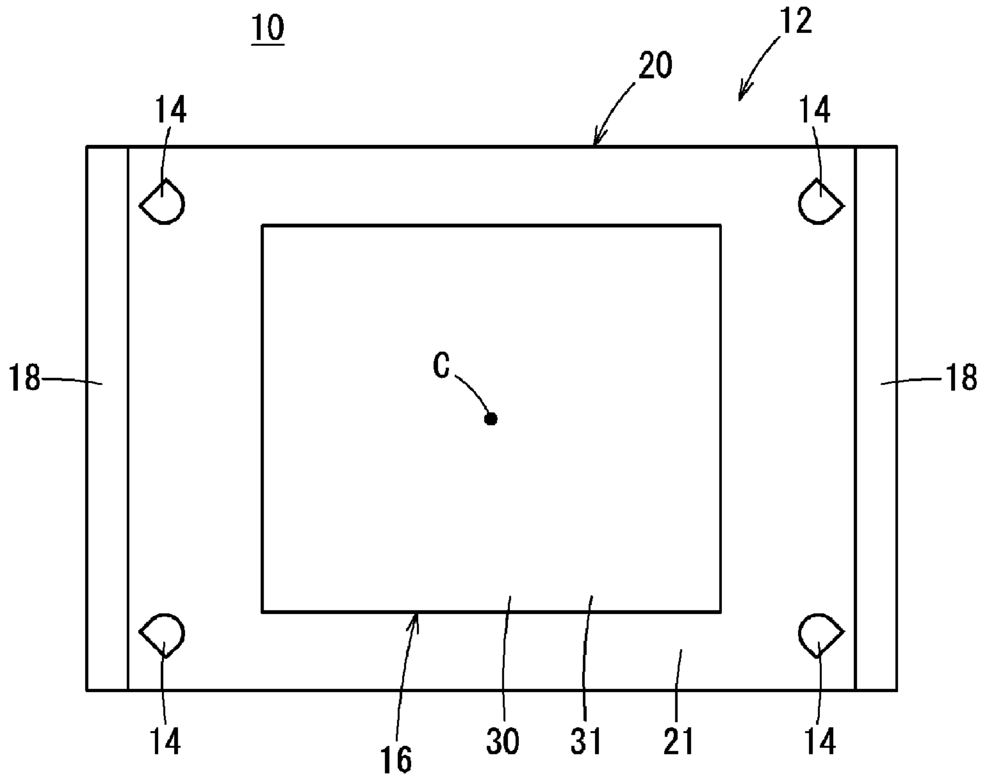
FIG. 3 is a bottom view of the blood vessel visualization apparatus in FIG. 1.

Furthermore, as illustrated in FIG. 3, the plurality of light sources 14 are preferably provided so as to surround the observation window 16. In the example illustrated in FIG. 3, the light sources 14 are respectively provided at four corners of the rectangular observation window 16. Each light source 14 is inclined such that the optical axis of each light source 14 is inclined toward the axis C of the observation window 16. The number of the light sources 14 to be arranged is not limited to four, and may be a number equal to or more than two. By providing the plurality of light sources 14 in this manner, a shadow of the medical tool 26 hardly appears when the medical tool 26 is arranged in the puncture space 27, so that it is possible to prevent visibility of the blood vessel 25 from lowering. Furthermore, the light source 14 may be arranged only on one side of the observation window 16 such as only on a left side or only on a right side of the observation window 16 in FIG. 3.

The observation window member 12 is provided with an unillustrated power supply circuit, and this power supply circuit turns on the light sources 14.

Note that the light sources 14 according to the present embodiment are not limited to the configuration provided to the frame member 20, and may be configured separately from the observation window member 12, and configured to be arranged between the frame member 20 and the visualization target site 24 immediately before use.

The blood vessel visualization apparatus 10 according to the present embodiment is configured as described above. Next, a blood vessel puncture system 40 will be described with reference to FIG. 4.

As illustrated in FIG. 4, the blood vessel puncture system 40 includes the blood vessel visualization apparatus 10, and the medical tool 26 that can puncture the visualization target site 24 of the living body. The medical tool 26 is, for example, a puncture needle or a catheter assembly, and includes a puncture portion 42 on a distal end side of the medical tool 26. A needle tip 44 that can perform puncturing subcutaneously is formed at a distal end of the puncture portion 42. The blood vessel visualization apparatus 10 is formed in such a size that the medical tool 26 can be arranged in the puncture space 27 between the visualization target site 24 and the observation window 16, and makes it possible to visually check the puncture portion 42 and the needle tip 44 through the observation window 16 when the medical tool 26 is operated in the puncture space 27.

The blood vessel visualization apparatus 10 and the blood vessel puncture system 40 according to the present embodiment are configured as described above, and effects thereof will be described below.

As illustrated in FIG. 4, the blood vessel visualization apparatus 10 is placed on the flat support base 22, and used. Prior to placement of the blood vessel visualization apparatus 10 on the support base 22, a patient's arm (visualization target site 24) is arranged on the support base 22. The observation window member 12 is arranged so as to cover an upper side of the visualization target site 24.

Subsequently, the light sources 14 of the observation window member 12 emit near infrared light. The near infrared light spreads in a gap between the light sources 14 and the visualization target site 24 with uniform luminance, is radiated on the visualization target site 24, and transmits to the inside of the visualization target site 24. The near infrared light is scattered and reflected in tissues of the living body, and the reflected near infrared light returns to the observation window 16. At this time, red blood cells in the blood vessel 25 in the living body absorb more near infrared light, and therefore a near infrared light image in which a portion of the blood vessel 25 is dark and other tissue portions are bright appears. The near infrared light image is converted into visible light by the wavelength conversion material of the observation window 16 and becomes visible.

The observation window 16 displays an image of the blood vessel 25 that is visualized by near infrared light, and is superimposed on the visualization target site 24 projected by light entering from the outside. Medical workers (users) such as doctors or nurses can reliably perform puncturing with the medical tool 26 such as the puncture needle or the catheter assembly based on the image of the blood vessel 25 projected on the observation window 16. The user can easily find the blood vessel 25 having an appropriate thickness suitable for puncturing based on the shape of the blood vessel 25 on the observation window 16. Furthermore, the user can directly visually check the visualization target site 24 through the observation window 16, and does not need to move a line of sight when performing puncturing, so that it is possible to more easily and reliably puncture the blood vessel 25 with the medical tool 26.

When the blood vessel 25 is visualized, for example, brightness in a room may be decreased or the surroundings of the observation window member 12 may be covered with a light shielding member as needed to limit the amount of visible light entering the visualization target site 24 in order to enhance the visibility of the blood vessel 25.

The blood vessel visualization apparatus 10, the blood vessel puncture system 40, and the observation window member 12 according to the present embodiment provide the following effects.

The blood vessel visualization apparatus 10 according to the present embodiment includes the light sources 14 that irradiate with near infrared light the visualization target site 24 at which the blood vessel 25 of the living body is visualized, the observation window 16 that contains the wavelength conversion material for converting the near infrared light into visible light, and visualizes a near infrared light image reflected from the visualization target site 24, and the support members 18 that support the light sources 14 and the observation window 16 such that the light sources 14 and the observation window 16 face and are spaced apart from the visualization target site 24.

The above blood vessel visualization apparatus 10 visualizes the blood vessel 25 based on the near infrared light reflected from the visualization target site 24 without using a complicated apparatus configuration such as an image capturing apparatus or a liquid crystal display apparatus. Furthermore, by arranging the light sources 14 and the observation window 16 facing the visualization target site 24 and spaced apart from the visualization target site 24, it is possible to obtain an image of the blood vessel 25 with high visibility while suppressing variations in the luminance.

In the above blood vessel visualization apparatus 10, the support members 18 may be configured to form the puncture space 27 in which the medical tool 26 can perform puncturing between the observation window 16 and the visualization target site 24. According to this configuration, the user can puncture the visualization target site 24 with the medical tool 26 while directly visually checking the medical tool 26 through the observation window 16. Consequently, the user can easily puncture the blood vessel 25 with the medical tool 26 without moving the line of sight.

In the above blood vessel visualization apparatus 10, the observation window 16 may be formed by applying the wavelength conversion material to the plate-like transparent material (resin or glass). Furthermore, the observation window 16 may be formed as a film-like wavelength conversion film containing the wavelength conversion material.

In the above blood vessel visualization apparatus 10, the observation window 16 may be transparent or semitransparent with respect to visible light, and makes it possible to visually check the visualization target site 24 through the observation window 16. According to this configuration, when puncturing is performed with the medical tool 26, the visualization target site 24 can be directly visually checked through the observation window 16, so that it is possible to more reliably perform puncturing with the medical tool 26.

In the above blood vessel visualization apparatus 10, the light shielding member may be provided in the surroundings of the light sources 14 and the observation window 16, and limit entry of visible light from the outside to the visualization target site 24. It is concerned that, when external light is too bright, the blood vessel 25 to be superimposed and displayed becomes difficult to see. However, according to the above configuration, it is possible to maintain visibility of the blood vessel 25 by limiting the entry of visible light.

In the above blood vessel visualization apparatus 10, the plurality of light sources 14 may be provided, and configured to irradiate the visualization target site 24 with near infrared light from a plurality of different directions. Consequently, it is possible to prevent the shadow of the medical tool 26 from being cast when the medical tool 26 is arranged in the puncture space 27.

The blood vessel puncture system 40 according to the present embodiment includes the above blood vessel visualization apparatus 10, and the medical tool 26 that includes the puncture portion 42 that can puncture the blood vessel 25. According to the blood vessel puncture system 40 employing this configuration, the blood vessel visualization apparatus 10 visualizes the blood vessel 25 with a simpler apparatus configuration.

In the above blood vessel puncture system 40, the medical tool 26 may be the puncture needle or the catheter assembly. According to this configuration, it is possible to puncture the blood vessel 25 suitable for puncturing while visually checking the blood vessel 25.

The observation window member 12 according to the present embodiment is the observation window member 12 of the blood vessel visualization apparatus 10 that includes the light sources 14 that irradiate with near infrared light the visualization target site 24 at which the blood vessel 25 of the living body is visualized, the observation window 16 that contains the wavelength conversion material for converting the near infrared light into visible light, and visualizes a near infrared light image reflected from the visualization target site 24, and includes the observation window 16 that is arranged facing the visualization target site 24, the frame member 20 that holds the observation window 16, and the support members 18 that support the frame member 20 such that the frame member 20 is spaced apart from the visualization target site 24. This configuration visualizes the blood vessel 25 of the visualization target site 24 with a simple apparatus configuration.

Second Embodiment

Figure 5:
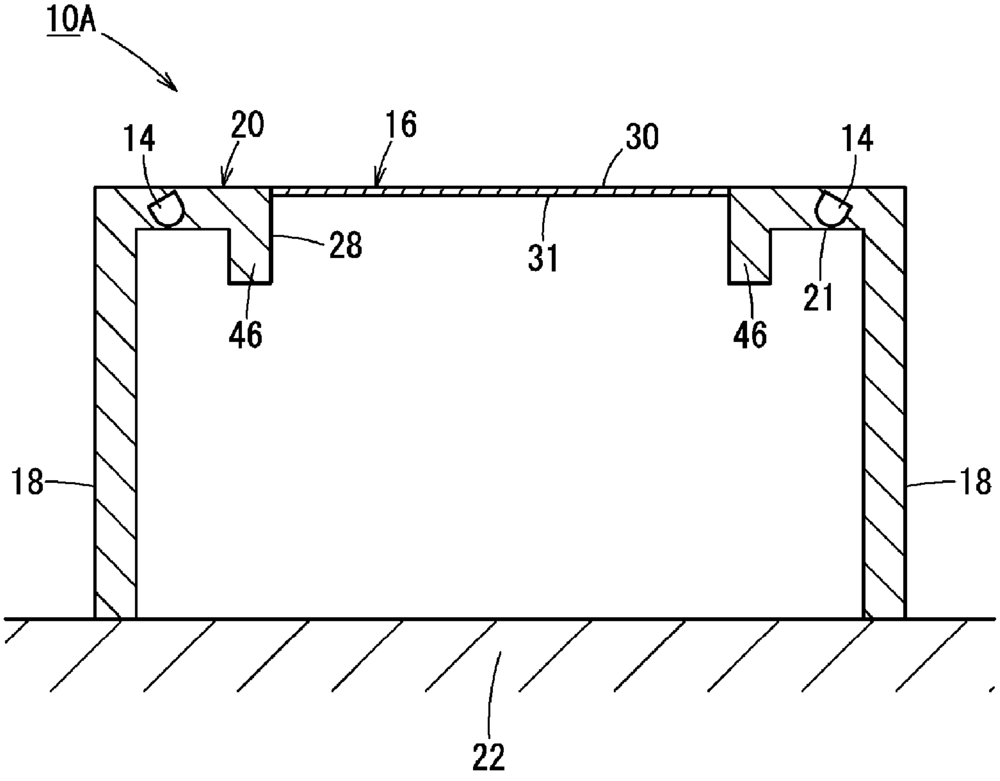
FIG. 5 is a cross-sectional view of a blood vessel visualization apparatus according to a second embodiment.

As illustrated in FIG. 5, a blood vessel visualization apparatus 10A according to the present embodiment includes partition walls 46 that are provided on a bottom surface 21 side of a frame member 20, and prevent irradiation light of light sources 14 that does not travel toward a visualization target site 24 from entering an observation window 16. In this regard, the same components of the blood vessel visualization apparatus 10A as those of a blood vessel visualization apparatus 10 illustrated in FIGS. 1 to 4 will be assigned the same reference numerals, and the detailed description thereof will be omitted.

The partition wall 46 is provided to partition the light source 14 and an observation window 16. More specifically, the partition wall 46 is provided along a periphery portion of an opening portion 28 of the frame member 20. The partition wall 46 is formed to protrude downward like a wall from the bottom surface 21 of the frame member 20.

The blood vessel visualization apparatus 10A according to the present embodiment provides the following effects.

In the blood vessel visualization apparatus 10A according to the present embodiment, the partition walls 46 are provided between the observation window 16 and the light source 14, and prevent near infrared light of the light sources 14 from directly entering the observation window 16. According to this configuration, it is possible to reduce entry of near infrared light that becomes noise, so that it is possible to more clearly project the blood vessel 25 on the observation window 16.

Although embodiments of the present invention have been described above with reference to preferred embodiments, the present invention is not limited to the above embodiments, and it goes without saying that various modifications can be made without departing from the gist of the present invention.

What is claimed is:

1. A blood vessel visualization apparatus comprising:
at least one light source configured to irradiate, with near infrared light, a visualization target site at which a blood vessel of a living body is to be visualized;
a plate-shaped frame member defining an opening;
an observation window fitted within the opening of the frame member, the observation window comprising:
a plate member, and
a wavelength conversion material configured to convert the near infrared light into visible light and to visualize a near infrared light image reflected from the visualization target site; and
at least one support member that supports the at least one light source and the frame member such that the at least one light source and the observation window face are spaced apart from the visualization target site, wherein:
the at least one light source is mounted on a bottom-surface side of the frame member such that near infrared light emitted from the at least one light source does not directly enter the observation window.

2. The blood vessel visualization apparatus according to claim 1, wherein:
the at least one support member is configured to form, between the observation window and the visualization target site, a puncture space that enables a medical tool to perform puncturing.

3. The blood vessel visualization apparatus according to claim 1, further comprising:
a partition wall located between the observation window and the at least one light source, and configured to prevent the near infrared light of the at least one light source from directly entering the observation window.

4. The blood vessel visualization apparatus according to claim 1, wherein:
the observation window comprises a film-like wavelength conversion film applied to a surface of the plate member and containing the wavelength conversion material.

5. The blood vessel visualization apparatus according to claim 1, wherein:
the observation window is transparent or semitransparent with respect to visible light.

6. The blood vessel visualization apparatus according to claim 1, further comprising:
a light shielding member surrounding the at least one light source and the observation window, and configured to limit entry of visible light from an outside to the visualization target site.

7. The blood vessel visualization apparatus according to claim 1, wherein:
the at least one light source comprises a plurality of the light sources configured to irradiate the visualization target site with the near infrared light from a plurality of different directions.

8. The blood vessel puncture system according to claim 7, wherein:
the at least one support member comprises a pair of support members across which the frame member bridges.

9. A blood vessel puncture system comprising:
the blood vessel visualization apparatus according to claim 1; and
a medical tool that includes a puncture portion configured to puncture a blood vessel.

10. The blood vessel puncture system according to claim 9, wherein:

the medical tool is a puncture needle or a catheter assembly.

11. The blood vessel puncture system according to claim 1, wherein:

the at least one support member comprises a pair of support members across which the frame member bridges.

12. The blood vessel puncture system according to claim 1, wherein:

a bottom surface of the plate member is recessed above a bottom surface of the frame member.

13. A method of visualizing a blood vessel of a living body, the method comprising:

providing a blood vessel visualization apparatus comprising:

at least one light source configured to emit near infrared light, a plate-shaped frame member defining an opening, an observation window fitted within the opening of the frame member, the observation window comprising:

a plate member, and a wavelength conversion material configured to convert the near infrared light into visible light, and at least one support member that supports the at least one light source and the observation window frame member, wherein:

the at least one light source is mounted on a bottom-surface side of the frame member such that near infrared light emitted from the at least one light source does not directly enter the observation window;

placing the blood vessel visualization apparatus such that the at least one light source and the observation window face are spaced apart from a visualization target site at which the blood vessel is to be visualized;

irradiating the visualization target site with the near infrared light from the light source;

visualizing, with the observation window, a near infrared light image reflected from the visualization target site; and puncturing the blood vessel with a puncture portion of a medical tool.

* * * * *